United States Patent [19]

Carney

[11] Patent Number: 5,081,230
[45] Date of Patent: Jan. 14, 1992

[54] MONOCLONAL ANTIBODIES REACTIVE WITH NORMAL AND ONCOGENIC FORMS OF THE RAS P21 PROTEIN

[75] Inventor: Walter P. Carney, Brighton, Mass.

[73] Assignee: E. I. DuPont DeNemours and Company, Wilmington, Del.

[21] Appl. No.: 71,175

[22] Filed: Jul. 8, 1987

[51] Int. Cl.$^5$ .................. C07K 15/28; C12N 5/20; A61K 39/395
[52] U.S. Cl. ................ 530/387; 435/240.27; 424/85.8
[58] Field of Search .............. 530/387; 424/85.8; 435/240.27

[56] References Cited

U.S. PATENT DOCUMENTS

| | | |
|---|---|---|
| 4,535,058 | 8/1985 | Weinberg et al. |
| 4,568,640 | 2/1986 | Rubin |
| 4,699,877 | 10/1987 | Cline et al. |
| 4,725,550 | 2/1988 | Perucho et al. |
| 4,762,706 | 8/1988 | McCormick et al. |
| 4,786,718 | 11/1988 | Weinberg et al. |
| 4,820,631 | 4/1989 | Lacal et al. |
| 4,871,838 | 10/1989 | Bos et al. |

FOREIGN PATENT DOCUMENTS

| | | |
|---|---|---|
| 108564 | 5/1984 | European Pat. Off. |
| 111823 | 9/1985 | European Pat. Off. |
| 111824 | 9/1985 | European Pat. Off. |
| 107244 | 12/1986 | European Pat. Off. |
| 259197 | 12/1985 | Japan |
| WO84/03087 | 8/1984 | PCT Int'l Appl. |
| WO85/00807 | 2/1985 | PCT Int'l Appl. |

OTHER PUBLICATIONS

Andreeff et al., Blood pp. 676–681, vol. 67, No. 3, Mar. 1986.
Barch et al., Cell Biology, Abstract #591, St. Louis, Mo. (1987).
Bizub et al., Oncogene, pp. 131–142, vol. 1, 1987.
CA 106;174296y, p. 550, vol. 106 (1987).
Carney et al., 78th Annual Mtg. of Amer. Assoc. for Cancer Research, May 20-23, 1987.
Carney et al., UCLA Symposia, Jan. 20-Feb. 15, 1986, Steamboat Springs Co; Alan N. Liss, Inc., N.Y. Journal of Cellular Biochemistry Suppl. 10A (1986).
Carney et al., 5th Annual Congress for Hybridoma Research, Jan. 26-29, 1986, Balt., Md.
Carney et al., Lab. Invest. 54-10A, Jan. 1986.
Carney et al., J. Cell. Bio. pp. 207-214, vol. 32 (1986).
Carney et al., Int'l., Academy of Pathology, Mar. 1987.
Carney et al., Third Annual Mtg on Oncogenes, 1987.
Carney et al., Monoclonal Antibodies & Cancer Therapy, pp. 565-572 (1985).
Carney et al., UCLA Symp. Mol. Cell. Biol., New Ser., pp. 565-572, vol. 27 (1985), CAS vol. 104 (1986), No. 166570B.
Caruso et al., Int. J. Cancer, pp. 587-595, vol. 38 (1986).
Chang et al., Nature, pp. 479-483, vol. 297, Jun. 10, 1982.
Carney et al., 69th Annual Mtg. of Federation of American Societies for Experimental Biology (FASEB), Apr. 1985.
Carney et al., Apr. 1986 Mtg of FASEB.
Carney et al., PNAS (U.S.A.), pp. 7485-7489, vol. 83, Oct. 1986.
Ward et al., "Comparative Immunohistochemical Reactivity of Monoclonal and Polyclonal Antibodies to H-ras p21 in Normal and Neoplastic Tissues of Rodents and Humans". Oncogene 4:203-213 (1989).

(List continued on next page.)

Primary Examiner—Margaret Moskowitz
Assistant Examiner—Denise Bernstein

[57] ABSTRACT

Monoclonal antibodies reactive with normal and oncogenic forms of the ras p21 protein. The antibodies are secreted by hybridomas obtained by immunizing mice with the Ha ras p21 protein containing the arginine mutation at position 12 of the protein. The antibodies and immunoreactive fragments thereof of useful for detection, diagnosis, quantitation, staging and classification of normal and activated ras p21s in normal tissues, malignant and premalignant lesions.

5 Claims, 1 Drawing Sheet

OTHER PUBLICATIONS

Sorrentino et al., "Preparation, Characterization, and Properties of Monoclonal Antibodies Against Intact H-ras p21 Proteins" Oncogene 4:215-221 (1989).

Hamer et al., "Production and Characterization of Anti--Ras p21 Monoclonal Antibodies", Draft Tentatively Accepted by Hybridoma, to be Published.

Furth et al., "Monoclonal Antibodies to the p21 Products of the Transforming Gene of Harvey Murine Sacroma Virus and of the Cellular ras Gene Family", pp. 294-304, Jul. 1982, vol. 43, No. 1, of Virology.

Hand et al., "Monoclonal Antibodies of Predefined Specificity Detect Activated ras Gene Expression in Human Mammary and Colon Carcinomas", pp. 5227-5231, Aug. 1984, vol. 81, PNAS.

Taparowsky et al., Banbury Report, 14:123-133 (1983), cited in Chem. Abstracts, CA 100(1):1425n.

Shimizu et al., Nature, 304(5926), 497-500 (1983), cited in Chem. Abstracts, 99(19):15309b.

Fasano et al. J. Mol. Appl. Genet., 2(2):173-180 (1983), cited in Chem. Abstracts, CA 99(19)153080v.

Tanaka et al., "Efficient Generation of Antibodies to Oncoproteins by Using Snythetic Peptide Antigens", pp. 3400-3404, May 1985, vol. 82, PNAS USA.

Tabin et al., "Mechanism of Activation of a Human Oncogene", pp. 143-149, Nov. 11, 1982, vol. 300, Nature.

Reddy et al., "A Point Mutation is Responsible for the Acquisition of Transforming Properties by T24 Human Bladder Carcinoma Oncogene", pp. 149-152, Nov. 11, 1982, vol. 300, Nature.

Yuasa et al., "Acquisition of Transforming Properties by Alternative Point Mutations with c-bas/has Human Proto-Oncogene", pp. 775-779, Jun. 30, 1983, vol. 303, Nature.

Bos et al., "Amino-Acid Substitutions at Codon 13 of the N-ras Oncogene in Human Acute Myeloid Leukaemia", pp. 726-730, Jun. 27, 1985, vol. 315, Nature.

Wong et al., "Detection of Activated $M_r 21,000$ Protein, the Product of ras Oncogenes, Using Antibodies with Specificity for Amino Acid 12", pp. 6029-6033, Dec. 1986.

Clanton et al., Mol. Cell. Biol. pp 3092-3097, vol. 7, No. 9, 1982.

Clark et al., PNAS (USA), pp. 5280-5284, vol. 82, No. 16, Aug. 1985.

Cooper et al., Biochimica et Biophysica Acta, pp. 9-20, vol. 738 (1984).

DeLellis et al., Intl. Academy of Pathology, Mar. 1987.

Der et al., Cell., pp. 167-176, vol. 44, Jan. 17, 1986.

Feramisco et al., Nature (England) 314 (6012):639-642, Apr. 18-24, 1985.

Finkel et al., Cell., pp. 151-158, vol. 37, May 1984.

Freedman et al., In Vitro Cellular Developmental Biology, pp. 621-624, vol. 22, No. 10, Oct. 1986.

Gallick et al., PNAS, pp. 1795-1799, vol. 82, Mar. 1985.

Gambke et al., Nature, pp. 476-478, vol. 307, Feb. 2, 1984.

Ghosh et al., J. Clin. Pathol. (England), pp. 428-434, vol. 39, No. 4, Apr. 1986.

Gibbs et al., PNAS (USA), pp. 5704-5708, vol. 81, Sep. 1984.

Hamer et al, Amer. Commercial & Industrial Conference & Expo. in Biotechnology, Apr. 27-May 1, 1986, Boston, Mass.

Herlyn et al., J. Clin. Immunology, pp. 135-140, vol. 2, No. 2 (1982).

Hirai et al., Nature, pp. 430-432, vol. 327, Jun. 4, 1987.

Ho et al., FASEB, vol. 46(3), 1987.

Kuzrock et al., Cancer Research, pp. 1530-1534, vol. 46, Mar. 1986.

Lacal et al., Mol. Cell Biol., vol. 6, No. 4, pp. 1002-1009, Apr. 1986.

Lee et al., Intl. Academy of Pathology, Mar. 1987.

Lefebvre et al., Lab. Invest, 54:35a, Jan. 1986.

Liu et al., Nature, pp. 186-188, vol. 330, Nov. 12, 1987.

Manne et al., PNAS (U.S.A.), pp. 376-380, vol. 82, Jan. 1985.

McGrath et al., Nature, pp. 644-649, vol. 310, Aug. 1984.

Metzgar et al., Cancer Research, pp. 601-608, vol. 42, Feb. 1982.

Moore et al., Nature, pp. 733-734, vol. 327, Jun. 25, 1987.

Niman et al., Clin. Lab. Med. (U.S.) 6(1):181-196, Mar. 1986.

Niman et al., Proc. Natl. Acad Sci. U.S.A., vol. 82, pp. 7924-7928, Dec. 1985.

Nishida et al., Biochem. Biophys. Res. Common. 146(1):247-252 (1987).

(List continued on next page.)

OTHER PUBLICATIONS

Nitta et al., Jpn. J. Cancer Research (Gann) pp. 21–26, vol. 78, Jan. 1987.
Ohuchi et al., Can. Res. 47(5):1413–1420 (1987).
Papageorge et al., J. Virol., pp. 509–519, vol. 44, No. 2, Nov. 1982.
Parada et al., Nature, pp. 474–476, vol. 297, Jun. 10, 1982.
Poe et al., J. Biol. Chem., pp. 3906–3909, vol. 260, No. 7, Apr. 10, 1985.
Radosevitch et al., Amer. Fed. Clin. Res., Chicago, Ill., Sep. 1987.
Robinson et al., Br. J. Cancer, pp. 877–883, vol. 54, 1986.
Santos et al., Science, pp. 661–664, vol. 223, Feb. 17, 1984.
Santos et al., Nature, pp. 343–344, vol. 298, Jul. 22, 1982.
Schlom, cited in the 5th Annual Congress for Hybridoma Research, pp. 165–166, Balt., Md., Jan. 26–29, 1986.
Scolnick et al., PNAS (U.S.A.), pp. 5355–5359, vol. 76, Oct. 1979.
Sevier et al., Clin. Chem., pp. 1797–1806, vol. 27, No. 11 (1981).
Shilo et al., Nature, pp. 607–609, vol. 289, Feb. 12, 1981.
Srivastava et al., Mol. Cell. Biol., pp. 3316–3319, vol. 5, No. 22, Nov. 1985.
Sweet et al., Nature, pp. 273–275, vol. 311, Sep. 1984.
Tahara et al., Jpn. J. Can. Res., pp. 517–522, 1986.
Tanaka et al., Can Res., pp. 1465–1470, vol. 46, Mar. 1986.
Thor et al., Nature, pp. 562–565, vol. 311, Oct. 11, 1984.
Trumpe et al., Third Ann. Mtg. on Oncogenes, 1987.
Wodnar–Felipowicz et al., Orcogene, pp. 457–461, vol. 1, No. 4 (1987).
Wolfe et al., Lab. Invest., 52:77a (1985).
Zarbl et al., Nature, pp. 382–385, vol. 315, May 30, 1985.
Taparowsky et al., Cell., pp. 581–586, vol. 34 (1983).

MONOCLONAL ANTIBODIES REACTIVE WITH NORMAL AND ONCOGENIC FORMS OF THE RAS P21 PROTEIN

FIELD OF INVENTION

This invention concerns murine monoclonal antibodies and fragments thereof that are immunoreactive with both normal forms of the ras protein (p21) and oncogenic forms of the ras protein. The oncogenic forms are found in a variety of malignant cells, both solid tumors and hematopoietic neoplasms. Also of concern are the hybridoma cell lines that secrete the antibodies, and use of the antibodies or antibody fragments of the invention for the detection, diagnosis, staging and classification of malignant and premalignant lesions.

BACKGROUND OF THE INVENTION

The immune response to entry of a foreign substance into the body consists of secretion by plasma cells of "antibodies" which are immunoglobulin (Ig) molecules with combining sites that recognize particular determinants on the surface of the foreign substance, or antigen, and bind specifically to them. Immunoglobulin is the generic name of various isotypes of antibodies that include IgG, IgM, IgA, IgE, and IgD. The various species of Ig have similarities and differences. For example, all immunoglobulin molecules have a constant portion, i.e., highly conserved (constant) amino acid sequence, within a particular Ig subclass (e.g., $IgG_1$). This constant region is responsible for various biological effector functions (e.g., complement activation). The portion of the immunoglobutin molecule responsible for immunological specificity (i.e., specific antigen binding) is called the variable region. It is made up of the variable regions of the Ig heavy and light chains. These variable regions differ in amino acid sequence according to the antigenic determinant which the Ig recognizes. Usually, the antibody (Ab) response to an antigen (Ag) is heterogenous. Upon injection of a body with an immunogen, the body manufactures large numbers of antibodies directed against various determinant sites on the antigen. It is difficult to separate antibodies from conventional antisera containing mixtures of antibodies. It has, therefore, long been a goal to design a continous source of defined antibodies that recognize and combine with specific antigen determinants.

Hybridoma technology concerns the fusion of myeloma cells with lymphocytes from animals which have been immunized with a particular antigen. The resulting hybridoma cell manufactures monoclonal antibodies that are specific against a single antigenic determinant. Monoclonal antibodies are begvginning to replace conventional antisera in standard diagnostic kits for such procedures as the radioimmunassay. Significant work is also being done to adapt hydridoma technology for therapeutic purposes.

Some properties that flow from an ideal hydridoma cell line are (1) high cloning efficiency; (2) the ability to grow rapidly in a medium supplemented with serum; (3) no secretion of myeloma immunoglobulin (Ig); (4) stable production of large amounts of Ig after fusion; and (5) ability to grow when reinserted into the originating species.

A typical procedure for making hydridomas is as follows: (a) immunize mice with a certain immunogen; (b) remove the spleens from the immunized mice and make a spleen suspension in an appropriate medium; (c) fuse the suspended spleen cells with mouse myeloma cells; (d) dilute and culture the mixture of unfused spleen cells, unfused myeloma cells and fused cells in a selective medium which will not support growth of the unfused myeloma cells or spleen cells; (e) evaluate the supernatant in each container containing hybridoma for the presence of antibody to the immunogen; and (f) select and clone hybridomas producing the desired antibodies. Once the desired hybridoma has been selected and cloned, the resultant antibody is produced by in vitro culturing of the desired hybridoma in a suitable medium. As an alternative method, the desired hybridoma can be injected directly into mice to yield concentrated amounts of antibody [Kennett, et al., (1981) Ed., *Monoclonal Antibodies*. Hybridomas: A new dimension in biological analyses, Plenum Press, New York].

Hybridomas produced by fusion of murine spleen cells and murine myeloma cells have been described in the literature by Kohler et al., in Eur. J. Immunol. 6, 511-519 (1976); by Milstein et al. in *Nature*, 266, 550 (1977); and by Walsh, *Nature*, 266, 550 (1977); and by Walsh, *Nature*, 266, 495 (1977).

The technique is also set out in some detail by Herzenberg and Milstein, in *Handbook on Experimental Immunology*, ed. Weir (Blackwell Scientific, London), 1979, pages 25.1 to 25.7 as well as in Kennett et al., supra.

Patents relating to monoclonal antibodies against human tumors produced by hybridoma technology include U.S. Pat. Nos. 4,182,124 and 4,196,265. Representative of the art concerning monoclonal antibodies that have specificity for antigens on carcinoma cells are U.S. Pat. No. 4,350,683.

Relative to the parent myeloma cell line employed herein for the fusion event, see Kearney et al., *Immunol.*, 123, 1548-1550 (1978).

Normal genes (DNA) encode proteins necessary for the growth, differentiation and survival of cells. Overexpression, mutation or expression of normal proteins at an inappropriate time in the cell cycle can transform normal cells to cancer cells. When normal genes act in this manner they are referred to as oncogenes.

Ras genes are found in a wide variety of nucleated mammalian cells and participate in normal cellular functions. The family of ras genes encode a series of immunologically related proteins with a molecular weight of 21,000 and are referred to as p21s. Ras genes present in mammalian cells have been demonstrated to be homologous to murine sarcoma viral oncogenes. (Weinberg, et al., U.S. Pat. No. 4,535,058: Harvey (1964), Nature. 104:1104: Kirsten et al. (1967). J.N.C.I., 39:311). Viral and cellular ras genes encode membrane bound proteins (Willingham, et al. (1980), Cell. 19:1005) which bind guanine nucleotides (Scolnick, et al. (1979) PNAS (U.S.A.), 76:5355: Papageorge, et al. (1982), J. Virol., 44:509: and Finek, et al. (1984), Cell. 37:151) and possess intrinsic GTPase activity (McGrath et al. (1984). Nature, 310:644: Sweet et al. (1984). Nature, 311:273; Gibbs et al. (1984) PNAS (U.S.A.) 81:5704; and Manne et al. (1985) PNAS 82:376).

DNA mediated transfection experiments using NIH3T3 cells as recipients have led to the identification of a family of activated transforming genes homologous to the ras genes of the Harvey (ras-H) and Kirsten (ras-K) sarcoma viruses. A third member of the ras family designated ras-N has been identified but has not been found to have a retroviral counterpart. Activated ras genes are structurally distinct from their normal homologs, having amino acid substitutions in the protein at positions 12, 13 or 61. (Tabin, et al. (1982), Nature, 300:143: Reddy et al. (1982) Nature, 300:149: Bos et al. (1985) Nature, 315:716; and Yuasa et al. (1983). Activated ras transoforming genes have been found in 10–20% of neoplasms including sarcomas, neuroblastomas, melanomas and carcinomas. In certain forms of leukemia activated ras genes and the corresponding proteins have been found in over 50% of the tumors studies. These activated ras genes and mutated proteins have also been found in established cell lines as well as primary and metastatic tumors.

The p21 ras protein in its normal nononcogenic nonactivated form contains the glycine amino acid at positions 12 and 13 and the glutamine amino acid at position 61.

Previous reports (Furth et al. (1982), J. Virol., 43:294) have described several rat monoclonal antibodies reactive with normal and activated or oncogenic (mutated) ras p21 proteins in yeast and mammalian cells. Other monoclonal antibodies generated by various methods have also been reported to react with the various forms of the ras p21 protein. Hand et al. Proc. Nat. Acad. Sci. U.S.A., Vol. 81, pp. 5227–5231 (1984); Thor et al., Nature, Vol. 311, pp. 562–565 (1984); Wong et al., Cancer Research, Vol. 46, pp. 6029–6033 (1986), and Tanaka, Proc. Natl. Acad. Sci., U.S.A., Vol. 82, pp 3400–3404 (1985).

STATEMENT OF DEPOSIT

Hybridoma cell lines which were found to secrete monoclonal antibodies reactive with normal and oncogenic forms of the ras p21 protein and the subject of this invention were deposited in the American Type Tissue Culture Collection (ATCC) under the Budapest Treaty. Hybridoma ras 8 was designated HB 9428, hybridoma ras 10 was designated HB 9426, and hybridoma ras 11 was designated HB 9427.

SUMMARY OF THE INVENTION

This invention provides mouse monoclonal antibodies and antibody fragments which specifically bind both normal ras protein (p21) and oncogenic forms of ras protein, such as the ras p21 protein which contains the amino acid arginine in place of glycine at position 12. The antibodies and antibody fragments of this invention are characterized in that, when tested in a microtitre plate-based ELISA under the standard conditions described below, they provide an optical density at 488 nm of between about 1.5 and about 2.5. The antibodies and antibody fragments of this invention are thus highly specific and sensitive diagnostic tools for the detection, quantitation, staging and classification of primary and metastatic neoplastic cells as well as preneoplastic lesions. Antibodies of the invention were produced by the procedure summarized below.

Mice designated Balb/c X C57 B1/6 were inoculated on several occasions with 100 micrograms of a recombinant ras p21 protein produced in bacteria. The immunogen p21 protein contained the arginine amino acid at position 12 instead of the glycine amino acid which is present in normal form of the protein. All three murine monoclonal antibodies that are the subject of this invention were raised by inoculating this p21 protein into mice.

Spleen from immune mice were fused with Sp/2-0 mouse myeloma cells and two weeks later culture supernatants were screened by enzyme-linked immunosorbent assay (ELISA) for reactivity with p21 proteins containing either arginine (immunogen) or glycine at position 12. Hybridomas secreting monoclonal antibodies ras 8, 10 and 11 were selected because of cross reactivity of the antibodies with both the activated (oncogenic) and normal ras p21 proteins.

Biochemical evaluation of a variety of human and rodent cell lines and tissues by immunoprecipitation and western blotting demonstrated the ability of ras 8, 10 and 11 to react with both activated and normal ras cellular proteins. Ras 8, 10 and 11 are also able to detect the H, K and N ras proteins. Thus monoclonal antibodies ras 8, 10 and 11 were selected because of the broad cross reactivity with cellular ras proteins.

Monoclonal antibody ras 10 is an IgG2a whereas monoclonal antibodies ras 8 and 11 are of the IgG2b subclass.

DETAILED DESCRIPTION OF THE INVENTION

Immunization

Figure 1:
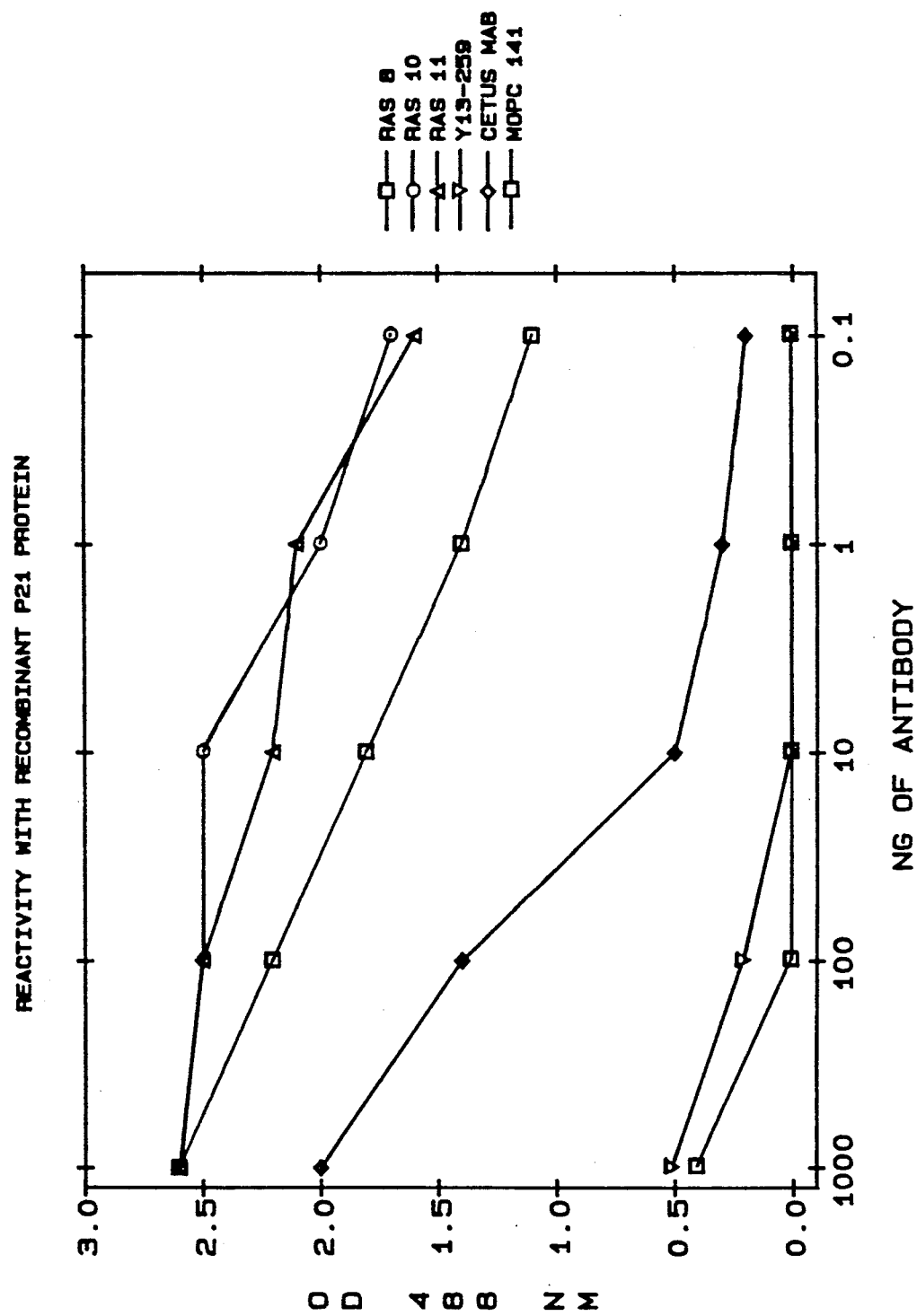

To produce murine monoclonal antibodies ras 8, 10 and 11 Balb/c X C57B1/6 mice were immunized intraperitoneally (i.p.) with 100 micrograms ($\mu$g) of a recombinant ras p21 protein produced in bacteria. The protein used for immunization was of the Harvey ras family and contained the amino acid arginine at position 12 instead of the normal amino acid glycine. Since the protein contained a mutation at position 12 the protein used for immunization is considered to be of the oncogenic or activated form. The first and second inoculations consisted of a mixture of complete Freunds Adjuvant and 100 $\mu$g of the activated p21. Subsequent inoculations given at two week intervals consisted only of the activated p21 protein.

Ras 8 was produced in fusion 351 (mouse 3103), ras 10 was produced in fusion 352 (mouse 3104) and ras 11 was produced in fusion 353 (mouse 3105).

Mouse serum was collected and evaluated by ELISA for the presence of anti-p21 antibody. Mice were selected for fusion based on the degree of serum reactivity to the immunogen. Three days before immune spleen cells were used for fusion, mice were given an i.p. boost with the immunogen.

Hybridoma Methodology

Three days after an i.p. boost with the p21 protein the spleen of the appropriate immune mouse was removed and fused with Sp2/0 cells. More particularly, after sacrifice of the mouse the spleen was removed, cells dispersed into a single cell suspension in serumless DMEM-high glucose medium. Spleen cells were mixed with Sp2/0 cells at a ratio of 4:1. This cell mixture was centrifuged at 1200×g for 10 minutes at room temperature. After removal of the supernatant, the cells were resuspended by gently tapping the tube. The fusion procedure was initiated by adding 1.0 ml of 45% w/v polyethylene glycol 3350 (BAKER) at 37 degrees over a 30 minute period. The cells were mixed occasionally with a pipette tip for 90 seconds and 5 ml of serumless DMEM medium was added over a 3 minute period. This was followed by the addition of 14 ml of DMEM medium supplemented with 10% fetal calf serum, L-glutamine, hypoxanthine, aminopterin and thymidine (HAT). The HAT medium was added over a 1 minute period (Kennett et al., supra).

Total volume was adjusted to 50 ml with HAT medium and the cells were centrifuged at 800×g for 7 minutes at room temperature. Supernatants were aspirated and the cell pellet disrupted with 10 ml of HAT medium. Five hundred thousand peritoneal cells were added. Cells were then pipetted into 96 well microtiter wells at a final concentration of two hundred thousand spleen cells per well. Approximately 14 days later, supernatants from wells containing hybridoma colonies were tested by ELISA for the desired reactivity with two types of p21 proteins. The two types were the normal form with glycine at position 12 of the protein and the activated form that contained arginine at position 12. Hybridomas producing the desired antibodies were cloned by limiting dilution such that 1 cell was plated for every 3 wells as described in Kennett et al., supra. Once colonies appeared (10-14 days later), the presence of antibody in the culture supernatant was determined by ELISA.

Hybridomas secreting the antibodies of interest were cloned two times and then inoculated into Pristane-primed mice for ascites production. Ascites fluid was then used to prepare purified immunoglobulin as described (Fahey, J., 1967, in Methods in Immunology and Immunochemistry, Vol. 1, pp. 307-334). Purified antibodies were determined by ELISA to be IgG kappa molecules using rabbit antibodies against various classes of mouse immunoglobulins.

ANTIBODY CHARACTERIZATION PROCEDURES

Analysis of Culture Supernatants

In order to select hybridomas secreting antibodies reactive with the bacterial p21s we evaluated culture supernatants from the hybridomas. Prior to screening hybridoma supernatants, 500 nanograms (ng) of bacterial produced p21s were dispensed to 96 well microtiter plates for overnight incubation at 37° C. The ras p21 proteins used in these tests were either the immunogen containing the arginine amino acid at position 12 or the normal protein containing the glycine amino acid at position 12. After overnight incubation plates were washed and the unbound sites on the plates were blocked with bovine serum albumin (BSA).

In order to select hybrids secreting antibodies with the desired reactivity thousands of culture fluids were tested. To do this 50 microliters (μl) of supernatant fluid was added to wells containing the p21 proteins. Supernatants were incubated overnight at 4 degrees. Next day the supernatant was removed and the wells were washed with BSA. Each well then received 50 μl containing 10 ng of goat anti-mouse IgG antibody conjugated to horseradish peroxidase (GAMHRP) diluted in BSA phosphate buffered saline (PBS). Wells were incubated for 60 minutes at 37 degrees. The GAMHRP was removed after incubation and wells were washed three times with the BSA-PBS mixture. The presence of bound GAMHRP was determined by adding 50 μl of the substrate o-phenylene diamine (OPD) in phosphate buffer containing 0.15% hydrogenperoxide. HRP in combination with its substrate (OPD) results in a yellow colored product. Development of the yellow product was allowed to occur at room temperature for 15 minutes. The enzymatic reaction was terminated by the addition of 50 μl of 4.5M $H_2SO_4$. Measurement of the resultant reaction product was accomplished by determining optical density (OD) at 488 nm. Presence of yellow color in the wells indicated that the mouse antibody was present in the hybridoma supernatant. This preliminary testing allowed us to select hybrids secreting antibodies ras 8, 10 and 11. As was previously described these hybrids were cloned, ascites produced and purified antibody produced for additional characterization. We next tested purified ras 8, 10 and 11 by ELISA on bacterial p21 proteins using the following STANDARD ELISA CONDITIONS: 500 ng of recombinant normal or oncogenic human ras protein per well as capture reagent; 0.1 to 1000 ng of the antibody or antibody fragment in 50 microliters per well of phosphate buffered saline (PBS) containing bovine serum albumin (BSA) as test sample; overnight incubation at 37° C. followed by BSA-PBS wash; 10 ng of goat anti-mouse IgG antibody conjugated to horseradish peroxidase in 50 microliters of BSA-PBS as detection reagent; 60 minute incubation at 37° C. followed by BSA-PBS wash; 50 microliters of o-phenylene diamine in PBS containing 0.15% hydrogen peroxide as substrate; 15 minute development, 50 microliters of 4.5M sulfuric acid as stop reagent; and determination of optical density (OD) at 488 nm. Referring to FIG. 1, the ELISA results show that with as little as 0.1 ng of antibody there is significant reactivity with the p21 protein; with 1 to 10 ng of antibody of per well an optical density in the range of about 1.5 to about 2.5 was obtained. FIG. 1 also shows results in which we compared the ras 8, 10 and 11 with two other anti-p21 monoclonal antibodies, Y13-259 and Cetus mouse MAB. Results show that the other antibodies were not as reactive as ras 8, 10 and 11. As a negative control MOPC 141, an antibody of the IgG2b subclass, was tested as well. Results demonstrate that the negative control was not at all reactive with the p21 protein. Y13-259 was tested at concentrations equivalent to the ras 8, 10 and 11 antibodies and was unreactive with the p21 protein. Additional studies demonstrated that Y13-259 does react with p21 proteins but it must be used at much higher concentrations than the ras reagents. In additional experiments we also determined that the ras antibodies react with a H-ras protein that contain various position 61 mutations. We noted, however, that the greatest reactivity was with the p21 used as the immunogen.

BIOCHEMICAL TESTING PROCEDURES

Immunoprecipitation

In order to select anit-ras p21 monoclonal antibodies that recognize cellular p21s in mammalian cells we performed the following tests. Purified antibodies 8, 10 and 11 were incubated in separate tubes with cells that had had their proteins radioactively labelled. Proteins in cells are labelled with an S-35 methionine amino acid by incubating the cells with this material overnight. As proteins are made they incorporate the radioactive methionine and therefore allow the protein to be detected. After the labelling period the cells were rinsed with PBS and solubilized with a 1% triton X-100 lysis buffer. The cells lysate was homogenized with a dounce homogenizer and centrifuged at 13,000 g for 15 minutes. The supernatant material contains the radioactive proteins of interest.

The purpose of the next set of tests was to determine whether ras 8, 10 and 11 could immunoprecipitate the radioactive ras p21s from various cells. To do this antibody was incubated with lysate containing radioactive proteins for 1 hour. During the 1 hour period p21 molecules bind to the highly specific anti-p21 monoclonal antibody. After the 1 hour incubation the p21 protein is bound to the anti-ras antibody. This material is then captured with a rabbit anti-mouse serum attached to Sepharose protein A beads. After the 1 hour to capture the antigen-antibody complex the material is centrifuged to sediment the Sepharose beads and anything attached to it. In this way we are able to capture the p21 from cell extracts. At the bottom of the tube is a complex consisting of Sepharose/protein A, rabbit anti-mouse sera, anti-p21 sera (ras 8, 10 or 11) and the p21 protein. This complex of materials is then boiled for three minutes in SDS to disrupt the various materials in the complex. The material is then centrifuged again to separate the Sepharose beads from the p21. The radioactively labelled p21 as well as other radioactive proteins are located in the supernatant and the heavier beads at the bottom of the tube. The supernatant material is then applied to a 12.5% polyacrylamide gel. Proteins are separated according to molecular weight by running an electric current through the gel. Once the electrophoresis is completed the presence of radioactive labelled proteins is detected by autoradiography.

Using this immunoprecipitation protocol it was determined that ras 8, 10 and 11 can immunoprecipitate a variety of cellular p21s. Results show that each of the antibodies when tested alone could immunoprecipitate both normal and activated (oncogenic) p21 proteins. Cell lines PSV-13 and NIH3T3 each contain the normal ras proteins. HT1080 contains an activated N-ras protein, NIH3T3 (SW480) contains an activated K-ras and NIH3T3 (EJ) contains activated H-ras protein. Therefore the ras 8, 10 and 11 antibodies were able to detect both normal and activated p21s therefore demonstrating their cross reactivity. Results also demonstrate that these antibodies can detect each of the three families of ras genes, H, K and N. Additional studies indicated that ras 10 was able to detect the N-ras product in HT1080 cells whereas the Y13-259 antibody was unable to do so when used at a comparable concentration as the ras 10. Ras 10 is therefore a more sensitive reagent or has greater specificity for p21s than Y13-259.

Western Blot

To determine whether ras 8, 10 and 11 could detect nonradioactive cellular p21s from cell lines and tissues a western blot procedure was performed.

Nonradioactive extracts of cells and tissues derived from humans and rodents were prepared in Triton X100 lysis buffer. For western blot analysis one mg of extracted material was applied to a 12.5% polyacrylamide gel and subjected to electrophoresis as described above. After electrophoresis the proteins on the gel were electrophoretically transferred to nitrocellulose membranes. After blocking the membranes with PBS containing 5% BSA they were incubated for one hour with 10 μg/ml of ras 8, 10 or 11. As negative control MOPC 141 or UPC-10 was used. Membranes were washed 3 times with PBS-NP-40 (0.05%), and incubated with goat anti-mouse HRP for 1 hour to detect the p21 mouse antibodies. Membranes were then washed 3 times with PBS-NP-40 and incubated with 4-chloro-1-napthol substrate to complete the reaction.

Results indicated that ras 8, 10 and 11 antibodies are highly sensitive for the detection of the ras protein in cell lines and human tumor tissues. In several instances the p21 was undetectable using the Y13-259 or Cetus anti-p21 antibodies whereas very prominent p21 bands were seen with ras 8, 10 and 11. Additional experiments were performed using human tumor samples. Under similar conditions the p21 band was undetectable with the Y13-259 antibody but readily detectable with the ras 10 antibody. Similar experiments were performed using the Cetus anti-p21 monoclonal antibody and it too was unable to detect the ras protein detectable by the ras 10 antibody. These results show that ras 8, 10 and 11 are superior antibodies to other commercially available reagents.

Electron Microscopy

In order to determine the location of the ras antibodies we employed the method of immunoelectron microscopy. In these tests we utilized a cell line known to be transformed by overexpression of the normal cellular Harvey Ras gene product. Results indicated ras antibody 11 bound to the membrane portion of the cell.

Immunohistochemistry

In this series of tests we evaluated the ras antibodies 8, 10 and 11 for their ability to detect the ras gene product by immunocytochemistry using an immunoperoxidase method described previously by HSU et al. 1981, J. Clin. Path. 75,734). The immunoperoxidase method employed an avidin-biotin complex.

These studies were first performed on cell lines that overexpressed the normal cellular Harvey ras gene product. Cell lines as well as fresh surgical specimens were formalin-fixed and embedded in paraffin prior to evaluation.

All three anti-ras monoclonal antibodies were able to stain a cell line transformed by overexpression of the normal ras gene. This cell line is designated PSV-13. Staining of the PSV-13 cells was confined to the inner plasma which is consistent with what is known about the ras protein. This staining of the PSV-13 cells could be blocked by preincubating the ras antibody with bacterially produced p21. Similar experiments were performed using human breast carcinomas and preincubation of antibody with immunogen decreased staining in a dose dependent fashion. These results demonstrate the specificity of the anti-ras monoclonal antibodies.

Detection of the Ras Protein in Culture Supernatants of Cancer Cells

The purpose of the next series of experiments was to determine whether the ras protein could be found in culture supernatants of a variety of tumor cell lines. Therefore in the next series of experiments we evaluated culture supernatants from cells transformed by overexpression of the normal ras protooncogene or NIH3T3 cells transformed with various activated ras genes and therefore expressing the mutated proteins.

In order to carry out this series of experiments we collected culture supernatants from cells several days after the cells were placed in cell culture. Various amounts of supernatant fluids were incubated with the ras 10 antibody as a first step in trying to immunoprecipitate the ras protein from solution. The procedure for immunoprecipitating the ras protein was as previously described. Results demonstrated that a ras p21 protein could be detected in a series of cell lines. In particular the PSV-13 cell contains the normal ras protein whereas the NIH3T3 (SW480) contains an activated ras protein that migrates electrophoretically different from that of the normal ras protein.

Immunoreactive Fragments

Immunoglobulins are composed of four chains. The chains of higher molecular weight are designated heavy (H) chains and those of lower molecular weight light (L) chains. Digestion of an immunoglobulin with proteolytic enzymes such as pepsin produces one F(ab)2 molecule and small peptides. The F(ab)2 portion is often referred to as an immunoreactive fragment. An immunoreactive fragment retains the biological activity and specificity of the parent immunoglobulin. Immunoreactive fragments will be used similarly to the parent immunoglobulin molecule. The advantage is they will reduce nonspecific background reactivity. If used in vivo, they will be less immunogenic and quite useful for immunotherapy. (Handbook of Experimental Immunology, Vol. 1.3d Ed., Edited by M. M. Weir, Immunochemistry, Blackwell Scientific Publications). This invention includes such immunoreactive fragments of the antibodies of the invention.

Flow Cytometry

Examination of ras p21 expression by flow cytometry using monoclonal antibody ras 10 permits direct measurement of p21 within individual cells. Several investigators have utilized Y13-259 (rat monoclonal anti-p21) to measure p21 levels in leukemic and transformed cell lines. We have used ras 10 which reacts with the three families of ras H, K, and N as well as both normal and activated p21s to measure intracellular p21 during lymphocyte activation.

Peripheral blood mononuclear cells were obtained from human donors and cultured in vitro either alone or in the presence of PHA (phytohemagglutinin) for 48 hours. After 48 hours cells were harvested from culture, washed, fixed in 1% formalin containing 0.24% saponin for 1 hour at 4° prior to staining for p21 with ras 10. After fixation cells were washed three times and incubated with 1 microgram of goat anti-mouse antibody labelled with fluorescein isothiocyanate.

Results showed that both populations of cells were positive for the ras p21. Greater than 90% of the cells in each group were stained specifically with ras 10, however the fluorescence intensity of cells cultured with PHA was much brighter than blood cells cultured without PHA. These results show that ras 10 specifically reacted with p21 from both PHA stimulated and unstimulated blood cells.

I claim:

1. A mouse monoclonal antibody or antibody fragment which specifically binds both normal ras protein (p21) and oncogenic forms of ras protein, characterized in that, when tested in a microtitre plate-based ELISA using the standard ELISA conditions described above, with 1 to 10 ng of the antibody or antibody fragment per well, the antibody or antibody fragment provides an optical density between about 1.5 and about 2.5.

2. A monoclonal antibody produced by a hybridoma cell line on deposit in the American Type Culture Collection (ATCC) with accession number HB 9426, HB 9427 or HB 9428, or a fragment of such an antibody which specifically binds both normal ras protein and oncogenic forms of ras protein.

3. A hybridoma capable of producing a monoclonal antibody as defined in claim 1.

4. A hybridoma on deposit with the ATCC with accession number HB 9426, HB 9427 or HB 9428.

5. A monoclonal antibody produced by a hybridoma cell line as defined in claim 4.

* * * * *